(12) United States Patent
Gandhi (10) Patent No.: US 6,911,430 B2
(45) Date of Patent: Jun. 28, 2005

(54) COMPOSITIONS AND METHODS FOR TREATING ILEUS

(75) Inventor: Salil Atul Gandhi, Chicago, IL (US)

(73) Assignee: VipoGen, LLC, Chicago, IL (US)

( * ) Notice: Subject to any disclaimer, the term of this patent is extended or adjusted under 35 U.S.C. 154(b) by 0 days.

(21) Appl. No.: 10/769,803

(22) Filed: Feb. 3, 2004

(65) Prior Publication Data

US 2005/0075290 A1 Apr. 7, 2005

Related U.S. Application Data

(60) Provisional application No. 60/507,122, filed on Oct. 1, 2003.

(51) Int. Cl.$^7$ ............................................... A61K 38/00
(52) U.S. Cl. ....................... 514/12; 530/350; 424/185.1
(58) Field of Search ........................... 514/12; 530/350; 424/185.1

(56) References Cited

U.S. PATENT DOCUMENTS

| | | | |
|---|---|---|---|
| 5,888,529 A | 3/1999 | Bunnett et al. | 424/422 |
| 5,929,035 A | 7/1999 | Owyang | 514/13 |
| 5,958,407 A | 9/1999 | Bunnett et al. | 424/94.64 |
| 6,197,333 B1 * | 3/2001 | Onyuksel et al. | 424/450 |
| 6,469,030 B2 | 10/2002 | Farrar et al. | 514/331 |
| 6,645,959 B1 | 11/2003 | Bakker-Arkema et al. | 514/215 |

OTHER PUBLICATIONS

Satoh, Y. et al. J. Smooth Muscle Res. 35(3):65–75 (1999).*
Bernstein, L.R. et al., "Current and Emerging Pharmacotherapy for Postoperative Ileus," Released Apr. 30, 2002, www.medscape.com.
Abad, C. et al., "Pituitary adenylate cyclase–activating polypeptide inhibits collagen–induced arthritis: an experimental immunomodulatory therapy." J. Immunol. vol. 167, pp. 3182–3189 (2001).
Adamou, J.E. et al., "Cloning and functional characterization of the human vasoactive intestinal peptide (VIP)–2 receptor." Biochem. Biophys. Res. Commun., vol. 209, pp. 385–392 (1995).
Alexandre, D. et al., "A cloned frog vasoactive intestinal polypeptide/pituitary adenylate cyclase–activating polypeptide receptor exhibits pharmacological and tissue distribution characteristics of both VPAC1 and VPAC2 receptors in mammals." Endocrinology vol. 140, pp. 1285–1293 (1999).
Almgren, M. et al., "Self–aggregation and phase behavior of poly(ethylene oxide)–pholy(propylene oxide)–oly(ethylene oxide) bloxk copolymers in aqueous solutions." Colloid Polym. Sci., vol. 273, pp. 2–15 (1995).
Andersson, A. et al., "Expression and Motor Effects of Secretin in Small and Large Intestine of the Rat." Peptides vol. 21, pp. 1687–1694 (2000).
Arimura, A., "Pituitary adenylate cyclase activating polypeptide (PACAP): discovery and current status of research." Regulatory Peptides vol. 37, pp. 287–303 (1992).

Bauer, F.E. et al., "Changes in the Blood Gas Concentration Caused by Secretin and Cholecystokinin: Indication of a Vasomotor Effect?" J. Clin. Gastroenterol., vol. 8, pp. 263–266 (1986).
Bayliss, W.M. et al., "The mechanism of pancreatic secretion," J. Physiol., vol. 28, pp. 325–353 (1902).
Bodansky, M. et al., "Conformation of Peptides of the Secretin–VIP–Glucagon Family in Solution." Peptides, vol. 7. Supp. 1, pp. 43–48 (1986).
Bodanszky, M. et al., "A preferred conformation in the vasoactive intestinal peptide (VIP). Molecular architecture of gastrointestinal hormones." Bioorgan. Chem., vol. 3, pp. 133–140 (1974).
Brizzolara, A.L. et al., "Endothelium–dependent and endothelium–independent vasodilatation of the hepatic artery of the rabbit," Br. J. Pharmacol. vol. 103, pp. 1206–1212 (1991).
Brunner, H. et al., "Secretin–Induced Bile Secretion, Bile Acid Output and Blood Supply to the Liver in the Dog," Eur. Surg. Res., vol. 7, pp. 205–211 (1975).
Carey, M.C. et al., "Micelle formation by the bile salts: physical–chemical and thermodynamic considerations," Arch. Inter. Med., vol. 130, pp. 506–527 (1972).
Carpenter, K.A. et al., "Aggregation Behaviour and $Zn^{2+}$ Binding Properties of Secretin," Biochemistry, vol. 37, pp. 16969–16974 (1998).
Cauvin, A. et al., "The novel VIP–like hypothalamic polypeptide PACAP interacts with high affinity receptors in the human neuroblastoma cell line NB–OK," Peptides, vol. 11, pp. 773–777 (1990).
Chang, C.H. et al., "Modulation of secretin release by neuropeptides in secretin–producing cells," Am. J. Physiol. vol. 275, pp. G192–202 (1998).
Chatterjee, T.K. et al., "Molecular cloning of a novel variant of the pituitary adenylate cyclase–activating polypeptide (PACAP) receptor that stimulates calcium influx by activation of L–type calcium channels," J. Biol. Chem., vol. 271, pp. 32226–32232 (1996).
Chez, M.G. et al., "Secretin and autism: a two–part clinical investigation," J. Autism. Dev. Disord., vol. 30, pp. 87–94 (2000).

(Continued)

Primary Examiner—Jon Weber
Assistant Examiner—Anand Desai
(74) Attorney, Agent, or Firm—Winston & Strawn LLP (57) ABSTRACT

The present invention is directed to compositions useful in treating or preventing ileus in a patient. The compositions of the invention include a pituitary adenylate cyclase activating peptide (PACAP) receptor antagonist and/or a vasoactive intestinal peptide (VIP) receptor antagonist in an amount sufficient to treat or prevent ileus in a patient. In one embodiment both a PACAP and VIP receptor antagonists are present, preferably in a combination that blocks vasoactive pituitary cyclase 1 (VPAC1), VPAC2 and pituitary adenylate cyclase 1 (PAC1) receptors. Methods of using such composition to treat or prevent ileus in a patient are also encompassed by the invention.

20 Claims, 2 Drawing Sheets

OTHER PUBLICATIONS

Chou, C.C. et al., "Comparison of vascular effects of gastrointestinal hormones on various organs," *Am. J. Physiol.*, vol. 232, pp H103–H109 (1977).

Chow, B.K. et al., "Molecular evolution of vertebrate VIP receptors and functional characterization of a VIP receptor from goldfish *Carassius auratus,*" *Gen. Comp. Endocrinol.*, vol. 105, pp. 176–185 (1997).

Couvineau, A. et al., "Human intestinal VIP receptor: Cloning and functional expression of two cDNA encoding proteins with different N–terminal domains," *Biochem. Biophys. Res. Commun.*, vol. 200, pp. 769–776 (1994).

Cullen J.J. et al., "Gastrointestinal peptide hormones during postoperative ileus. Effect of octreotide," *Dig. Dis. Sci.*, vol. 39, No. 6, pp. 1179–1184 (1994).

Daniel P.B. et al., "Novel alternatively spliced exon in the extracellular ligand–binding domain of the pituitary adenylate cyclase–activating polypeptide (PACAP) type 1 receptor (PAC1R) selectively increases ligand affinity and alters signal transduction coupling during spermatogenesis," *J. Biol. Chem.*, vol. 276, pp. 12938–12944 (2001).

Dautzenberg F.M. et al., "N–terminal splice variants of the type I PACAP receptor: isolation, characterization and ligand binding/selectivity determinants," *J. Neuroendocrinol.*, vol. 11, pp. 941–949 (1999).

Davis, M.J. et al., "Microvascular pressure distribution and responses of pulmonary allografts and cheek pouch arterioles in the hamster to oxygen," *Circ. Res.*, vol. 49, pp. 125–132 (1981).

De Winter, B.Y. et al., "Effect of adrenergic and intrergic blockade on experimental ileus in rats," *Br. J. Pharmacol.*, vol. 120, pp. 464–468 (1997).

De Winter B.Y. et al., "Role of VIP1/PACAP receptors in postoperative ileus in rats," *Br. J. Pharmacol.* vol. 124, No. 6, pp. 1181–1186 (1998).

Dickinson, T. et al., "Evidence for roles of vasoactive intestinal polypeptide (VIP) and pituitary adenylate cyclase activating polypeptide (PACAP) receptors in modulating the responses of rat dorsal horn neurons to sensory inputs," *Neuropeptides,* vol. 31, pp. 175–185 (1997).

Dow, R.C. et al., "Pituitary adenylate cyclase–activating peptide–38 (PACAP)–38 is released into hypophysial portal blood in the normal male and female rat," *J. Endocrinol.*, vol. 42, pp. R1–4 (1994).

Espat, N.J. et al., "Vasoactive intestinal peptide and substance P receptor antagonists improve postoperative ileus," *J. Surg. Res.*, vol. 58, No. 6, pp. 719–723 (Jun. 1995).

Filizola, M. et al., "Conformational study of vasoactive intestinal peptide by computational methods," *J. Pept.*, vol. 50, pp. 55–64 (1997).

Fisher Surface Tensiomat Model 21 Catalog No. 14–814 Instruction manual.

Gandhi, S. et al., "Interactions of human secretin with sterically stabilized phospholipid micelles amplify peptide–induced vasodilation in vivo," *Peptides,* vol. 23, pp. 1433–1439 (2002).

Gandhi S. et al., "Increased bioactivity of secretin in sterically stabilized micelles: Implication for therapy," *Int. Symp. Controlled Release,* vol. 28, pp. 572–573 (2001).

Gandhi, S. et al., "Secretin self–assembles and interacts spontaneously with phospholipids in vitro," *Peptides,* vol. 23, pp. 201–204 (2002).

Ganea, D. et al., "Neuropeptides as modulators of macrophage functions. Regulation of cytokine production and antigen presentation by VIP and PACAP," *Arch. Immunol. Ther. Exp.*, vol. 49, pp. 101–110 (2001).

Gao, X. et al., "Vasoactive intestinal peptide encapsulated in liposomes: Effects on systemic arterial blood pressure," *Life Sci.*, vol. 54, pp. PL247–PL252 (1994).

Gao, X. et al., "Short–term exposure to lipopolysaccharide is associated with microvascular contractile dysfunction in vivo," *Life. Sci.*, vol. 56, pp. 1243–1249 (1995).

Gardiner, S.M. et al., "Regional haemodynamic responses to PACAP and VIP in conscious rats," *Br. J. Pharmacol.*, vol. 111, pp. 589–597 (1994).

Gaw, A. J. et al., Relaxation of sheep cerebral arteries by vasoactive intestinal polypeptide and neurogenic stimulation: inhibition by L–$N^G$–monomethyl arginine in endothelium–denuded vessels. *Br. J. Pharmacol.*, vol. 102, pp. 367–372 (1991).

Gololobov, G. et al., "Stabilization of vasoactive intestinal peptide by lipids," *J. Pharmacol. Exp. Ther.*, vol. 285, pp. 753–758 (1998).

Gottschall, P.E. et al., "Hypothalamic binding sites for pituitary adenylate cyclase activating polypeptide: characterization and molecular identification," *FASEB J.*, vol. 5, pp. 194–199 (1991).

Greaves R.R.S.H. et al., The differential effect of VIP and PACAP on guinea pig gallbladder in vitro. *Eur. J. Gastro. Hepat.*, vol. 12, pp. 1181–1184 (2000).

Greenfield, N.J., "Methods to estimate the conformation of proteins and polypeptides from circular dichroism data," *Anal. Biochem.*, vol. 235. pp. 1–10 (1996).

Haghjoo, K. et al., "Solution structure of vasoactive intestinal peptide (11–28)–$NH_2$, a fragment with analgesic properties,"*Pept. Res.*, vol. 9, pp. 327–331 (1996).

Hashimoto, H. et al., "Molecularcloning and tissue distribution of a receptor for pituitary adenylate cyclase activating polypeptide," *Neuron.*, vol. 11, pp. 333–342 (1993).

Hjelm, Jr., R.P. et al., Organization of phosphatidylcholine and bile salt in rodlike mixed micelles. *J. Phys. Chem.*, vol. 96, pp. 8653–8661 (1992).

Hofmann M. et al., "Conformation of secretin in dimethyl sulfoxide solution: NMR studies and restrained molecular dynamics," *Eur. J. Biochem.*, vol. 186, pp. 95–103 (1989).

Hosoya, M. et al., "Molecular cloning and functional expression of rat cDNAs encoding the receptor for pituitary adenylate cyclase activating polypeptide (PACAP)," *Biochem. Biophys. Res. Commun.*, vol. 194, pp. 133–143 (1993).

Ignarro, L.J. et al., "Mechanisms of endothelium–dependent vascular smooth muscle relaxation elicited by bradykinin and VIP," *Am. J. Physiol.*, vol. 253 (Heart Circ. Physiol. 22), pp. H1074–H1082 (1987).

Ikezaki, H. et al., "Vasodilation elicited by liposomal VIP is unimpeded by anti–VIP antibody in hamster cheek pouch," *Am. J. Physiol.*, vol. 275, pp. R56–R62 (1998).

Inooka, H., et al., "Pituitary adenylate cyclase activating polypeptide (PACAP) with 27 residues. Conformation determined by 1H NMR and CD spectroscopies and distance geometry in 25% methanol solution," *Int. J. Pept. Protein Res.*, vol. 40, pp. 456–464 (1992).

Juarranz, M.G. et al., "Vasoactive intestinal polypeptide $VPAC_1$ and $VPAC_2$ receptor chimeras identify domains responsible for the specificity of ligand binding and activation," *Eur. J. Biochem.*, vol. 265, pp. 449–456 (1999).

Kobayashi, H. et al., "Pituitary adenylate cyclase activating polypeptides (PACAPs) increase camp in rat cerebral microvessels", *Brain Research* vol. 647, pp. 145–147 (1994).

Lee, S. et al., Effects of salts on conformational changes of basic amphipathic peptides from β–structure to β –helix in the presence of phospholipid liposomes and their channel–forming ability. *Biochim. Biophys. Acta.,* vol. 1151, pp. 76–82 (1993).

Lenard, Jr., L. et al., "Inhibitory effect of PACAP(6–38) on relaxations induced by PACAP, VIP and non–adrenergic, non–cholinergic nerve stimulation in the guinea–pig *Taenia caeci,*" *Naunyn–Schmiedeberg's Arch Pharmacol* vol. 361, pp. 492–497 (2000).

Leyton, J. et al., "PACAP(6–38) is a PACAP receptor antagonist for breast cancer cells," *Breast Cancer Res. Treat.,* vol. 56, pp. 177–186 (1999).

Li, P. et al., "A secretin releasing peptide exists in dog pancreatic juice," *Life Sci.,* vol. 66, pp. 1307–1316 (2000).

Lutz, E.M. et al., "The VIP2 receptor: Molecular characterization of a cDNA encoding a novel receptor for vasoactive intestinal peptide," *FEBS 13195.,* vol. 334, No. 1, pp. 3–8 (1993).

Martinez, C. et al., "Anti–inflammatory role in septic shock of pituitary adenylate cyclase–activating polypeptide receptor," *PNAS,* vol. 99, No. 2, pp. 1053–1058 (2002).

Masuo, Y. et al., "Effects of vasoactive intestinal polypeptide (VIP) and pituitary adenylate cyclase activating polypeptide (PACAP) on the spontaneous release of acetylcholine from the rat hippocampus by brain microdialysis," *Brain Res.,* vol. 611, pp. 207–215 (1993).

Metz, D.C. et al., "A randomized controlled crossover study comparing synthetic porcine and human secretins with biologically derived porcine secretin to diagnose Zollinger–Ellson Syndrome," *Aliment Pharmacol Ther* vol. 15, pp. 669–676 (2001).

Montero, M. et al., "Molecular evolution of the growth hormone–releasing hormone/pituitary adenylate cyclase–activating polypeptide gene family. Functional implication in the regulation of growth hormone secretion," *J. Mol. Endocrinol.,* vol. 25, pp. 157–168 (2000).

Moody, T.W. et al., "A vasoactive intestinal peptide antagonist inhibits non–small cell lung cancer growth," *Proc. Natl. Acad. Sci. USA,* vol. 90, pp. 4345–4349 (1993).

Morrow, J.A. et al., "Molecular cloning and expression of a cDNA encoding a receptor for pituitary adenylate cyclase activating polypeptide (PACAP)," *FEBS 12869,* vol. 329, pp. 99–105 (1993).

Muranushi, N. et al., "Effects of fatty acids and monoglycerides on permeability of lipid bilayer," *Chemistry and Physics of Lipids,* vol. 20, pp. 269–279 (1981).

Naruse, S. et al., "Vasodilator Effect of Pituitary Adenylate Cyclase Activating Polypeptide (PACAP) on Femoral Blood Flow in Dogs," *Peptides,* vol. 14, pp. 505–510 (1993).

Noda, Y. et al., "Partitioning of vasoactive intestinal polypeptide into lipid bilayers," *Biochem. Biophys. Acta.,* vol. 1191, pp. 324–330 (1994).

Onyuksel, H. et al., "Surface–active properties of vasoactive intestinal peptide," *Peptides,* vol. 21, pp. 419–423 (2000).

Onyuksel, H. et al., "A novel formulation of VIP in sterically stabilized micelles amplifies vasodilation in vivo," *Pharm. Res.,* vol. 16, pp. 155–160 (1999).

Pantaloni, C. et al., "Alternative splicing in the N–terminal extracellular domain of the pituitary adenylate cyclase–activating polypeptide (PACAP) receptor modulates receptor selectivity and relative potencies of PACAP–27 and PACAP–38 in phospholipase C activation," *J. Biol. Chem.,* vol. 271, No. 36, pp. 22146–22151 (1996).

Patel, M, et al., "Simplified preparation of vasoactive intestinal peptide in sterically stabilized liposomes," *Int. Symp. Controlled Release,* vol. 24, pp. 913–914 (1997).

Pisegna, J.R. et al., "Molecular cloning and functional expression of the pituitary adenylate cyclase–activating polypeptide type I receptor," *Proc. Natl. Acad. Sci.,* vol. 90, pp. 6345–6349 (1993).

Raud, J., "Intravital microscopic studies on acute mast cell–dependent inflammation," *Acta. Physiol. Scand. Suppl.,* vol. 578, pp. 1–58 (1989).

Robberecht, P. et al., "PACAP and VIP receptors in rat liver membranes," *Am. J. Physiol.,* vol. 260, pp. G97–102 (1991).

Robinson, R.M. et al., "Lipid–induced conformational changes in glucagon, secretin, and vasoactive intestinal peptide," *Biopolymers,* vol. 21, pp. 1217–1228 (1982).

Rubinstein, I. et al., "Conformation and Vasoreactivity of VIP in phospholipids: effects of calmodulin," *Peptides,* vol. 20, pp. 1497–1501 (2000).

Rubinstein, I. et al., "L–Arginine dilates cheek pouch arterioles in hamsters with hereditary cardiomyopathy," *J. Lab. Clin. Med.,* vol. 125, pp. 313–318 (1995).

Said, S.I., "VIP as a modulator of lung inflammation and airway constriction," *Am. Rev. Dis.,* vol. 143, pp. S22–S24 (1991).

Schuster, T.G. et al., "Postoperative ileus after abdominal surgery", *Urology,* vol. 59, No. 4, pp. 465–471 (2001).

Schutt C., "Secretin and Autism: A Clue But Not a Cure", *Newsletter Nat. Alliance for Autism Res.,* No. 4, pp. 21–25 (1998).

Sejourne, F. et al., "Development of a novel bioactive formulation of vasoactive intestinal peptide in sterically stabilized liposomes," *Pharm. Res.,* vol. 14, pp. 362–365 (1997).

Sejourne, F. et al., "Mechanisms of vasodilation elicited by VIP in sterically stabilized liposomes in vivo," *Am. Physiol. Soc.,* vol. 273, pp. R287–292 (1997).

Sreerama, N. et al., "Estimation of protein secondary structure from circular dichroism spectra: inclusion of denatured proteins with native proteins in the analysis," *Anal. Biochem.,* vol. 287, pp. 243–251 (2000).

Sreerama, N. et al., "Estimation of protein secondary structure from circular dichroism spectra: comparison of CONTIN, SELCON, and CDSSTR methods with an expanded reference set," *Anal. Biochem.,* vol. 287, pp. 252–260 (2000).

Suda, K. et al., "Investigation of the interaction of VIP binding sites with VIP and PACAP in human brain," *Neurosci. Lett.,* vol. 137, pp. 19–23 (1992).

Suzuki, H. et al., "Neutral endopeptidase modulates vasoactive intestinal peptide–induced vasodilation in situ," *Am. J. Physiol.,* vol. 271 (Regulatory Integrative Comp. Physiol. 0): R393–R397 (1996).

Suzuki, H. et al., "Encapsulation of vasoactive intestinal peptide into liposomes: effects on vasodilation in vivo," *Life Sci,* vol. 57, pp. 1451–1457 (1995).

Suzuki, H. et al., "Encapsulation of vasoactive intestinal peptide into liposomes restores vasorelaxation in hypertension in situ," *Am. J. Physiol.,* vol. 271 (Heart Circ. Physiol. 40): H282–H287 (1996).

Taguchi, A. et al., "Selective Postoperative Inhibition of Gastrointestinal Opioid Receptors," *N. Engl. J. Med.,* vol. 345, No. 13, pp. 935–940 (2001).

Tatsuno, I. et al., "Neuropeptide regulation of interleukin–6 production from the pituitary: stimulation by pituitary adenylate cyclase activating polypeptide and calcitonin gene–related peptide," *Endocrinology,* vol. 129, pp. 1797–1804 (1991).

Tornoe, K. et al., "PACAP–1(1–38) as a neurotransmitter in pig pancreas: receptor activation revealed by the antagonist PACAP–6(6–38)," *Am. J. Physiol.,* vol. 273, pp. G436–G446 (1997).

Trubetskoy, V. et al., "Stable polymeric micelles: lymphagiographic contrast media for gamma scintigraphy and magnetic resonance imaging," *Acad. Radiol.,* vol. 3, pp. 232–238 (1996).

Trubetskoy, V.S. et al., "Use of polyoxyethylene–lipid conjugate as long–circulating carriers for delivery of therapeutic and diagnostic agents," *Advan. Drug Deliv. Reviews,* vol. 16, pp. 311–320 (1995).

Uddman, R. et al., "Pituitary adenylate cyclase activating polupeptide (PACAP), a new vasoactive intestinal peptide (VIP)–like peptide in the respiratory tract," *Cell Tissue Res.,* vol. 265, pp. 197–201 (1991).

Ulrich II, C.D. et al., "Secretin and Vasoactive Intestinal Peptide Receptors: Members of a Unique Family of G Protein–Coupled Receptors," *Gastroenterology,* vol. 114, pp. 382–397 (1998).

Vaudry, D. et al., "Pituitary Adenylate Cyclase–Activating Polypeptide and Its Receptors: From Structure to Function," *Pharm Rev.,* vol. 52, pp. 269–324 (2000).

Verine, H.J. et al., "Subcutaneous Secretin in Dogs: Influence of Solvent and Volume of Solvent," *Acta. Hepato.–Gastroenterol.,* vol. 22, pp. 35–40 (1974).

Wilmore, D. W. et al., "Management of patients in fast track surgery," *BMJ,* vol. 322, pp. 473–479 (2001).

Woodle, M.C. et al., "Prolonged systemic delivery of peptide drugs by long circulating liposomes: illustration with vasopressin in the Brattleboro rat," *Pharm. Res.,* vol. 9, pp. 260–265 (1992).

Wray, V. et al., "Solution structure comparison of the VIP/PACAP Family of Peptides by NMR Spectroscopy," *Annals NY Acad Sci.,* pp. 37–44.

Wray, V. et al., "Solution structure of pituitary adenylate cyclase activating polypeptide by nuclear magnetic resonance spectroscopy," *Biochemistry,* vol. 32, pp. 5832–5841 (1992).

Xia, W.J. et al., "Mechanistic studies on surfactant–induced membrane permeability enhancement," *Pharm. Res.,* vol. 17, pp. 612–618 (2000).

Yokoyama, M. et al., "Preparation of adriamycin–conjugated poly(ethyleneglycol)–poly (aspartic acid) block copolymer," *Makromol Chem Rapid Commun,* vol. 8, pp. 431–435 (1987).

\* cited by examiner

SEQUENCE LISTING

<160> NUMBER OF SEQ ID NOS: 12

<210> SEQ ID NO 1
<211> LENGTH: 38
<212> TYPE: PRT
<213> ORGANISM: Homo sapiens

<400> SEQUENCE: 1

His Ser Asp Gly Ile Phe Thr Asp Ser Tyr Ser Arg Tyr Arg Lys Gln
1               5                   10                  15

Met Ala Val Lys Lys Tyr Leu Ala Ala Val Leu Gly Lys Arg Tyr Lys
            20                  25                  30

Gln Arg Val Lys Asn Lys
        35

<210> SEQ ID NO 2
<211> LENGTH: 28
<212> TYPE: PRT
<213> ORGANISM: Homo sapiens

<400> SEQUENCE: 2

His Ser Asp Ala Val Phe Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 3
<211> LENGTH: 28
<212> TYPE: PRT
<213> ORGANISM: Homo sapiens

<400> SEQUENCE: 3

Lys Pro Arg Arg Pro Tyr Thr Asp Asn Tyr Thr Arg Leu Arg Lys Gln
1               5                   10                  15

Met Ala Val Lys Lys Tyr Leu Asn Ser Ile Leu Asn
            20                  25

<210> SEQ ID NO 4
<211> LENGTH: 28
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Phe can be D-p-Cl-Phe

<400> SEQUENCE: 4

His Ser Asp Ala Val Phe Thr Asp Asn Tyr Thr Arg Leu Arg Lys Gln
1               5                   10                  15

Leu Ala Val Lys Lys Tyr Leu Asn Ser Ile Leu Asn
            20                  25

<210> SEQ ID NO 5
<211> LENGTH: 18
<212> TYPE: PRT
<213> ORGANISM: Homo sapiens
<220> FEATURE:
<221> NAME/KEY: misc_feature
<222> LOCATION: (13)..(13)
<223> OTHER INFORMATION: Xaa is Diphenylalanine

<400> SEQUENCE: 5

```
Phe Thr Asp Tyr Tyr Thr Arg Leu Arg Lys Gln Met Xaa Val Lys Lys
1               5                   10                  15

Tyr Leu

<210> SEQ ID NO 6
<211> LENGTH: 23
<212> TYPE: PRT
<213> ORGANISM: Homo sapiens
<220> FEATURE:
<221> NAME/KEY: misc_feature
<222> LOCATION: (13)..(13)
<223> OTHER INFORMATION: Xaa is Diphenylalanine

<400> SEQUENCE: 6

Phe Thr Asp Tyr Tyr Thr Arg Leu Arg Lys Gln Met Xaa Val Lys Lys
1               5                   10                  15

Tyr Leu Asn Ser Ile Leu Asn
            20

<210> SEQ ID NO 7
<211> LENGTH: 20
<212> TYPE: PRT
<213> ORGANISM: Homo sapiens

<400> SEQUENCE: 7

Asn Ser Tyr Arg Lys Val Leu Gly Gln Leu Ser Ala Arg Lys Leu Leu
1               5                   10                  15

Gln Asp Ile Met
            20

<210> SEQ ID NO 8
<211> LENGTH: 25
<212> TYPE: PRT
<213> ORGANISM: Homo sapiens
<220> FEATURE:
<221> NAME/KEY: misc_feature
<222> LOCATION: (1)..(1)
<223> OTHER INFORMATION: His can be Ac-His
<220> FEATURE:
<221> NAME/KEY: misc_feature
<222> LOCATION: (2)..(2)
<223> OTHER INFORMATION: Phe can be D-Phe

<400> SEQUENCE: 8

His Phe Val Phe Thr Asn Ser Tyr Arg Lys Val Leu Gly Gln Lys Arg
1               5                   10                  15

Ala Arg Lys Leu Leu Gln Asp Ile Leu
            20                  25

<210> SEQ ID NO 9
<211> LENGTH: 29
<212> TYPE: PRT
<213> ORGANISM: Homo sapiens
<220> FEATURE:
<221> NAME/KEY: misc_feature
<222> LOCATION: (1)..(1)
<223> OTHER INFORMATION: Tyr can be N-Ac-Tyr
<220> FEATURE:
<221> NAME/KEY: misc_feature
<222> LOCATION: (2)..(2)
<223> OTHER INFORMATION: Phe can be D-Phe

<400> SEQUENCE: 9

Tyr Phe Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg
```

```
                    20              25

<210> SEQ ID NO 10
<211> LENGTH: 30
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa can be absent, His or Tyr
<220> FEATURE:
<221> NAME/KEY: MISC_FEATURE
<222> LOCATION: (2)..(2)
<223> OTHER INFORMATION: Xaa can be absent, Ser, Ala or D-Arg
<220> FEATURE:
<221> NAME/KEY: MISC_FEATURE
<222> LOCATION: (3)..(3)
<223> OTHER INFORMATION: Xaa can be absent or Asp
<220> FEATURE:
<221> NAME/KEY: MISC_FEATURE
<222> LOCATION: (4)..(4)
<223> OTHER INFORMATION: Xaa can be absent, Gly, Ala or Cys
<220> FEATURE:
<221> NAME/KEY: MISC_FEATURE
<222> LOCATION: (5)..(5)
<223> OTHER INFORMATION: Xaa can be absent, Ile, Val or Thr
<220> FEATURE:
<221> NAME/KEY: MISC_FEATURE
<222> LOCATION: (8)..(8)
<223> OTHER INFORMATION: Xaa can be Asp, Ser, Glu or Asn
<220> FEATURE:
<221> NAME/KEY: MISC_FEATURE
<222> LOCATION: (9)..(9)
<223> OTHER INFORMATION: Xaa can be Ser, Asn, Glu or Asp
<220> FEATURE:
<221> NAME/KEY: MISC_FEATURE
<222> LOCATION: (10)..(10)
<223> OTHER INFORMATION: Xaa can be Tyr or Leu
<220> FEATURE:
<221> NAME/KEY: MISC_FEATURE
<222> LOCATION: (11)..(11)
<223> OTHER INFORMATION: Xaa can be Ser, Thr or Arg
<220> FEATURE:
<221> NAME/KEY: MISC_FEATURE
<222> LOCATION: (12)..(12)
<223> OTHER INFORMATION: Xaa can be Arg or Lys
<220> FEATURE:
<221> NAME/KEY: MISC_FEATURE
<222> LOCATION: (13)..(13)
<223> OTHER INFORMATION: Xaa can be Tyr, Leu or Val
<220> FEATURE:
<221> NAME/KEY: MISC_FEATURE
<222> LOCATION: (14)..(14)
<223> OTHER INFORMATION: Xaa can be Arg, Leu or Gln
<220> FEATURE:
<221> NAME/KEY: MISC_FEATURE
<222> LOCATION: (15)..(15)
<223> OTHER INFORMATION: Xaa can be Lys, Gly, Cys, Ala or Glu
<220> FEATURE:
<221> NAME/KEY: MISC_FEATURE
<222> LOCATION: (16)..(16)
<223> OTHER INFORMATION: Xaa can be Gln, Ala, Lys or Gly
<220> FEATURE:
<221> NAME/KEY: MISC_FEATURE
<222> LOCATION: (17)..(17)
<223> OTHER INFORMATION: Xaa can be Met, Leu, Ile or Ala
<220> FEATURE:
<221> NAME/KEY: MISC_FEATURE
<222> LOCATION: (18)..(18)
<223> OTHER INFORMATION: Xaa can be Ala, Ser or Arg
<220> FEATURE:
<221> NAME/KEY: MISC_FEATURE
<222> LOCATION: (19)..(19)
<223> OTHER INFORMATION: Xaa can be Val, Ala, Gln or Leu
<220> FEATURE:
<221> NAME/KEY: MISC_FEATURE
<222> LOCATION: (20)..(20)
<223> OTHER INFORMATION: Xaa can be Lys, Gln or Arg
```

```
<220> FEATURE:
<221> NAME/KEY: MISC_FEATURE
<222> LOCATION: (21)..(21)
<223> OTHER INFORMATION: Xaa can be Lys or Arg
<220> FEATURE:
<221> NAME/KEY: MISC_FEATURE
<222> LOCATION: (22)..(22)
<223> OTHER INFORMATION: Xaa can be Tyr or Leu
<220> FEATURE:
<221> NAME/KEY: MISC_FEATURE
<222> LOCATION: (24)..(24)
<223> OTHER INFORMATION: Xaa can be Ala, Asn, Glu or Gln
<220> FEATURE:
<221> NAME/KEY: MISC_FEATURE
<222> LOCATION: (25)..(25)
<223> OTHER INFORMATION: Xaa can be Ala, Ser, Gly or Asp
<220> FEATURE:
<221> NAME/KEY: MISC_FEATURE
<222> LOCATION: (26)..(26)
<223> OTHER INFORMATION: Xaa can be Val, Ile, Leu
<220> FEATURE:
<221> NAME/KEY: MISC_FEATURE
<222> LOCATION: (27)..(27)
<223> OTHER INFORMATION: Xaa can be Leu, Ile, Val or Met
<220> FEATURE:
<221> NAME/KEY: MISC_FEATURE
<222> LOCATION: (28)..(28)
<223> OTHER INFORMATION: Xaa can be Gly, absent, Asn or Ser
<220> FEATURE:
<221> NAME/KEY: MISC_FEATURE
<222> LOCATION: (29)..(29)
<223> OTHER INFORMATION: Xaa can be Lys, absent, Ser or Arg
<220> FEATURE:
<221> NAME/KEY: MISC_FEATURE
<222> LOCATION: (30)..(30)
<223> OTHER INFORMATION: Xaa can be Arg, absent or Gln

<400> SEQUENCE: 10

Xaa Xaa Xaa Xaa Xaa Phe Thr Xaa Xaa Xaa Xaa Xaa Xaa Xaa Xaa Xaa
1               5                   10                  15

Xaa Xaa Xaa Xaa Xaa Xaa Leu Xaa Xaa Xaa Xaa Xaa Xaa Xaa
            20                  25                  30

<210> SEQ ID NO 11
<211> LENGTH: 44
<212> TYPE: PRT
<213> ORGANISM: Homo sapiens

<400> SEQUENCE: 11

Tyr Ala Asp Ala Ile Phe Thr Asn Ser Tyr Arg Lys Val Leu Gly Gln
1               5                   10                  15

Leu Ser Ala Arg Lys Leu Leu Gln Asp Ile Met Ser Arg Gln Gln Gly
            20                  25                  30

Glu Ser Asn Gln Glu Arg Gly Ala Arg Ala Arg Leu
        35                  40

<210> SEQ ID NO 12
<211> LENGTH: 44
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa can be Tyr or His
<220> FEATURE:
<221> NAME/KEY: MISC_FEATURE
<222> LOCATION: (2)..(2)
<223> OTHER INFORMATION: Xaa can be Ala, Val or Ser
<220> FEATURE:
<221> NAME/KEY: MISC_FEATURE
<222> LOCATION: (4)..(4)
<223> OTHER INFORMATION: Xaa can be Ala, Gly or Asp
```

-continued

```
<220> FEATURE:
<221> NAME/KEY: MISC_FEATURE
<222> LOCATION: (5)..(5)
<223> OTHER INFORMATION: Xaa can be Ile, Leu or Met
<220> FEATURE:
<221> NAME/KEY: MISC_FEATURE
<222> LOCATION: (6)..(6)
<223> OTHER INFORMATION: Xaa can be Phe or Leu
<220> FEATURE:
<221> NAME/KEY: MISC_FEATURE
<222> LOCATION: (7)..(7)
<223> OTHER INFORMATION: Xaa can be Thr, Ser Asn or Asp
<220> FEATURE:
<221> NAME/KEY: MISC_FEATURE
<222> LOCATION: (8)..(8)
<223> OTHER INFORMATION: Xaa can be Asn, Ser, Thr, Lys or Arg
<220> FEATURE:
<221> NAME/KEY: MISC_FEATURE
<222> LOCATION: (9)..(9)
<223> OTHER INFORMATION: Xaa can be Ser, Asn, Ala or Asp
<220> FEATURE:
<221> NAME/KEY: MISC_FEATURE
<222> LOCATION: (10)..(10)
<223> OTHER INFORMATION: Xaa can be Tyr or Leu
<220> FEATURE:
<221> NAME/KEY: MISC_FEATURE
<222> LOCATION: (12)..(12)
<223> OTHER INFORMATION: Xaa can be Lys, Arg, Asp or Asn
<220> FEATURE:
<221> NAME/KEY: MISC_FEATURE
<222> LOCATION: (13)..(13)
<223> OTHER INFORMATION: Xaa can be Val, Ile, Leu, Ala, or Tyr
<220> FEATURE:
<221> NAME/KEY: MISC_FEATURE
<222> LOCATION: (15)..(15)
<223> OTHER INFORMATION: Xaa can be Gly, Ser or Val
<220> FEATURE:
<221> NAME/KEY: MISC_FEATURE
<222> LOCATION: (18)..(18)
<223> OTHER INFORMATION: Xaa can be Ser, Tyr or Arg
<220> FEATURE:
<221> NAME/KEY: MISC_FEATURE
<222> LOCATION: (20)..(20)
<223> OTHER INFORMATION: Xaa can be Arg or Gln
<220> FEATURE:
<221> NAME/KEY: MISC_FEATURE
<222> LOCATION: (21)..(21)
<223> OTHER INFORMATION: Xaa can be Lys, Asn or Arg
<220> FEATURE:
<221> NAME/KEY: MISC_FEATURE
<222> LOCATION: (22)..(22)
<223> OTHER INFORMATION: Xaa can be Leu, Val, Tyr or Phe
<220> FEATURE:
<221> NAME/KEY: MISC_FEATURE
<222> LOCATION: (23)..(23)
<223> OTHER INFORMATION: Xaa can be Leu or Ile
<220> FEATURE:
<221> NAME/KEY: MISC_FEATURE
<222> LOCATION: (24)..(24)
<223> OTHER INFORMATION: Xaa can be Gln or His
<220> FEATURE:
<221> NAME/KEY: MISC_FEATURE
<222> LOCATION: (25)..(25)
<223> OTHER INFORMATION: Xaa can be Asp, Glu, Ser, Thr or Trp
<220> FEATURE:
<221> NAME/KEY: MISC_FEATURE
<222> LOCATION: (26)..(26)
<223> OTHER INFORMATION: Xaa can be Ile or Leu
<220> FEATURE:
<221> NAME/KEY: MISC_FEATURE
<222> LOCATION: (27)..(27)
<223> OTHER INFORMATION: Xaa can be Met or Thr
<220> FEATURE:
<221> NAME/KEY: MISC_FEATURE
<222> LOCATION: (28)..(28)
<223> OTHER INFORMATION: Xaa can be Ser, Asn or Ala
<220> FEATURE:
<221> NAME/KEY: MISC_FEATURE
<222> LOCATION: (29)..(29)
```

```
<223> OTHER INFORMATION: Xaa can be Arg, Lys or Val
<220> FEATURE:
<221> NAME/KEY: MISC_FEATURE
<222> LOCATION: (30)..(30)
<223> OTHER INFORMATION: Xaa can be Gln, Arg or His
<220> FEATURE:
<221> NAME/KEY: MISC_FEATURE
<222> LOCATION: (31)..(31)
<223> OTHER INFORMATION: Xaa can be Gln, Val or Leu
<220> FEATURE:
<221> NAME/KEY: MISC_FEATURE
<222> LOCATION: (33)..(33)
<223> OTHER INFORMATION: Xaa can be Glu, Gly or Ala
<220> FEATURE:
<221> NAME/KEY: MISC_FEATURE
<222> LOCATION: (34)..(34)
<223> OTHER INFORMATION: Xaa can be Ser, Arg, Ala, Val, Gly or Glu
<220> FEATURE:
<221> NAME/KEY: MISC_FEATURE
<222> LOCATION: (35)..(35)
<223> OTHER INFORMATION: Xaa can be Asn, Ile, Ser or Glu
<220> FEATURE:
<221> NAME/KEY: MISC_FEATURE
<222> LOCATION: (36)..(36)
<223> OTHER INFORMATION: Xaa can be Gln, Ser, Met, Thr or Glu
<220> FEATURE:
<221> NAME/KEY: MISC_FEATURE
<222> LOCATION: (37)..(37)
<223> OTHER INFORMATION: Xaa can be Glu, Ser, Ile, Met or Asp
<220> FEATURE:
<221> NAME/KEY: MISC_FEATURE
<222> LOCATION: (38)..(38)
<223> OTHER INFORMATION: Xaa can be Arg, Gln, Leu or Glu
<220> FEATURE:
<221> NAME/KEY: MISC_FEATURE
<222> LOCATION: (39)..(39)
<223> OTHER INFORMATION: Xaa can be Gly, Arg, Glu or Asp
<220> FEATURE:
<221> NAME/KEY: MISC_FEATURE
<222> LOCATION: (40)..(40)
<223> OTHER INFORMATION: Xaa can be Ala, Pro, Ser or Asp
<220> FEATURE:
<221> NAME/KEY: MISC_FEATURE
<222> LOCATION: (41)..(41)
<223> OTHER INFORMATION: Xaa can be Arg, Lys, Glu, Asp, Asn, Thr or Ser
<220> FEATURE:
<221> NAME/KEY: MISC_FEATURE
<222> LOCATION: (42)..(42)
<223> OTHER INFORMATION: Xaa can be Ala, Val, Ser, Phe, Leu or absent
<220> FEATURE:
<221> NAME/KEY: MISC_FEATURE
<222> LOCATION: (43)..(43)
<223> OTHER INFORMATION: Xaa can be Arg, Val, Asn, Ser or Glu
<220> FEATURE:
<221> NAME/KEY: MISC_FEATURE
<222> LOCATION: (44)..(44)
<223> OTHER INFORMATION: Xaa can be Leu, Arg, Pro or absent

<400> SEQUENCE: 12

Xaa Xaa Asp Xaa Xaa Xaa Xaa Xaa Xaa Xaa Arg Xaa Xaa Leu Xaa Gln
 1               5                  10                  15

Leu Xaa Ala Xaa Xaa Xaa Xaa Xaa Xaa Xaa Xaa Xaa Xaa Xaa Xaa Gly
            20                  25                  30

Xaa Xaa Xaa Xaa Xaa Xaa Xaa Xaa Xaa Xaa Xaa Xaa
            35                  40
```

COMPOSITIONS AND METHODS FOR TREATING ILEUS

CROSS-REFERENCE TO RELATED APPLICATION

This application claims priority to U.S. Provisional Patent Application No. 60/507,122, filed Oct. 1, 2003, the disclosure of which is expressly incorporated herein by reference thereto.

TECHNICAL FIELD

The invention relates generally to a composition for treating or preventing ileus in a patient, the composition including a pituitary adenylate cyclase activating peptide (PACAP) receptor antagonist or a vasoactive intestinal peptide (VIP) receptor antagonist. In a preferred embodiment the composition comprises both a PACAP and a VIP receptor antagonist in an amount sufficient to treat or prevent ileus in a patient. Methods of using such composition to treat or prevent ileus in a patient are also encompassed by the invention.

BACKGROUND OF THE INVENTION

It is a common problem for patients having undergone surgical procedures, especially surgery of the abdomen, to suffer from a particular bowel dysfunction called postoperative ileus (POI). "Ileus", as used herein, refers to the obstruction of the bowel or gut, especially the colon. See, e.g., Dorland's Illustrated Medical Dictionary, p. 816, 27th ed. (W.B. Saunders Company, Philadelphia 1988). Ileus should be distinguished from constipation, which refers to infrequent or difficulty in evacuating the feces. See, e.g., Dorland's Illustrated Medical Dictionary, p. 375, 27th ed. (W.B. Saunders Company, Philadelphia 1988). Ileus may be diagnosed by the disruption of normal coordinated movements of the gut, resulting in failure of the propulsion of intestinal contents. See, e.g., Resnick, J., Am. J. of Gastroenterology 1997, 92, 751 and Resnick, J., Am. J. of Gastroenterology, 1997, 92, 934. In some instances, particularly following surgery, including surgery of the abdomen, the bowel dysfunction may become quite severe, lasting for more than a week and affecting more than one portion of the GI tract. This condition is often referred to as postoperative paralytic ileus and most frequently occurs after laparotomy (see Livingston, E. H. and Passaro, E. D. Jr., Digestive Diseases and Sciences 1990, 35, 121). Similarly, postpartum ileus is a common problem for women in the period following childbirth.

Currently, therapies for treating ileus include functional stimulation of the intestinal tract, stool softeners, laxatives, lubricants, intravenous hydration, nasogatric suction, prokinetic agents, early enteral feeding, nasogastric decompression, and the use of less invasive surgical procedures. These prior art methods suffer from drawbacks, for example, as lacking specificity for POI or post-partum ileus. And these prior art methods offer no means for prevention. If ileus could be prevented or more effectively treated, hospital stays, recovery times, and medical costs would be significantly decreased in addition to the benefit of minimizing patient discomfort. Adolor Corporation is presently in phase III clinical trials for a therapy to treat Postoperative ileus using Alvimopan (Entereg®). Adolor's therapy, however, utilizes opiod receptor antagonists, as opposed the present invention, which involves the use of PACAP and VIP receptor antagonists.

SUMMARY OF THE INVENTION

The invention relates to a composition for treating or preventing ileus in a patient. The composition generally comprises a pituitary adenylate cyclase activating peptide (PACAP) receptor antagonist or a vasoactive intestinal peptide (VIP) receptor antagonists that is VIP(10–28) (SEQ ID NO:2, residues 10–28). Preferably the PACAP receptor antagonists or VIP receptor antagonists is in an amount sufficient to treat or prevent ileus.

In a preferred embodiment the composition comprises a PACAP receptor antagonists and a VIP receptor antagonist. In this embodiment of the invention it is preferable if the combined amount of PACAP and VIP receptor antagonists is sufficient to treat or prevent ileus in a patient.

The amount of PACAP and VIP receptor antagonists are typically between 0.001 and 5000 μg per kg body weight of the patient being treated. In a preferred embodiment the antagonists are in an amount equal to between 50 μg and 500 μg per kg body weight of the patient being treated.

In another preferred embodiment, the composition further includes a carrier, preferably a pharmaceutically suitable carrier. Sterically stabilized micelles (SSM), sterically stabilized liposomes (SSL), or mixed micelles are examples of suitable carriers.

Preferably, the PACAP receptor antagonist is selected from a group consisting of PACAP(6–38) (SEQ ID NO:1, residues 6–38); PACAP(6–27) (SEQ ID NO:1, residues 6–27); analogues of PACAP receptor antagonists (SEQ ID NO:10) and combinations thereof and the VIP receptor antagonist is selected from a group consisting of VIP(6–28) (SEQ ID NO:2, residues 6–28); VIPhyb (SEQ ID NO:3); [D-p-Cl-Phe$^6$, Leu$^{17}$]VIP (SEQ ID NO:4); [Tyr$^9$, Dip$^{18}$]VIP (6–23) (SEQ ID NO:5); [Tyr$^9$,Dip$^{18}$]VIP(6–28) (SEQ ID NO:6); GH-releasing factor-(8–27)NH$_2$ (SEQ ID NO:7); GHRH analogues with VIP receptor binding properties (SEQ ID NO:12); [Ac-His$^1$, D-Phe$^2$, Lys$^{15}$, Arg$^{16}$, Leu$^{25}$] VIP(3–7)/GRF(8–27) (SEQ ID NO:8); [N-Ac-Tyr$^1$, D-Phe$^2$]-GRF(1–29)NH$_2$ (SEQ ID NO:9); VIP(10–28) (SEQ ID NO:2, residues 10–28); VIP(11–28) (SEQ ID NO:2, residues 11–28); [Ac-Try$^1$, D-Phe$^2$]-GRF(1–29) amide; and combinations thereof.

Also, preferbly the VIP antagonist is VIP(10–28) (SEQ ID NO:2, residues 10–28) and the PACAP antagonist is PACAP (6–38) (SEQ ID NO:1, residues 6–38). Preferably, the VIP and PACAP receptor antagonists included in the composition jointly inhibit binding of native peptides to vasoactive pituitary cyclase 1 (VPAC$_1$) receptors, VPAC$_2$ receptors and pituitary adenylate cyclase 1 (PAC$_1$) receptors.

The present invention is also directed to a method for treating or preventing ileus in a patient. The method comprises administering to a patient in need of such treatment the composition described above. In this embodiment of the invention the PACAP and/or VIP antagonist typically are administered in an amount effective to activate or augment intestinal transit in the patient.

The compositions of the invention are generally administered intravenously, intra-arterially, intra-nasally, aerosol administration, nebulization, inhalation, insufflation, intratracheally, intraarticularly, orally, transdermally, subcutaneously, or topically onto mucous membranes. In a preferred embodiment the composition is administered intravenously or orally. Preferably the patient is a human and treatment is for postoperative ileus or paralytic ileus, wherein the composition is administered pre-operatively, intra-operatively, post-operatively, or a combination thereof.

BRIEF DESCRIPTION OF THE DRAWINGS

Values are mean±.SD; *P<0.05 in comparison to distance traveled following skin incision only. +P<0.05 in comparison to distance traveled following skin incision followed by laparotomy and manipulation of intestines. @P<0.05 in comparison to distance traveled following skin incision followed by laparotomy and manipulation of intestines and treatment with either VIP or PACAP receptor antagonists or combinations thereof (VIP10–28 or PACAP6–38, respectively).

FIG. 2 shows the effect of receptor antagonists on the % Evan's Blue traveled in the intestines of Wistar rats. Values are mean±.SEM; *P<0.05 in comparison to % traversed following skin incision only. +P<0.05 in comparison to % traversed following skin incision followed by laparotomy and manipulation of intestines. @P<0.05 in comparison to % traversed following skin incision followed by laparotomy and manipulation of intestines and treatment with either VIP or PACAP receptor antagonists or combinations thereof (VIP10–28 or PACAP6–38, respectively).

DETAILED DESCRIPTION OF THE PREFERRED EMBODIMENTS

The present invention is directed to compositions and methods for the treatment or prevention of ileus. Different types of ileus may be treated and/or prevented using the methods of the invention. The methods are particularly suitable for treating and/or preventing postoperative ileus, postpartum ileus, paralytic ileus. "Postoperative ileus" (POI), which may follow surgery such as laparotomy, may be characterized by such symptoms as, for example, obstruction of the gut, particularly in the colon, resulting in nausea, vomiting, lack of passage of flatus and/or stools, abdominal distention and lack of bowel sounds. This condition generally lasts from about 2 to about 5 days, but may endure longer, including up to about one week. Longer durations are generally characteristic of a more severe form of ileus, termed postoperative paralytic ileus, which may affect other portions of the GI tract in addition to the colon.

"Post-partum ileus" generally refers to obstruction of the gut, particularly the colon, following parturition. Both natural and surgically assisted procedures during parturition may lead to postpartum ileus treated by the present invention. Symptoms of post-partum ileus and postoperative ileus are similar. "Paralytic ileus" refers to the general condition in which peristalsis stops, i.e., paralysis of the bowel wall, resulting in the obstruction of the bowel.

The term "patient" refers to animals, including mammals, preferably humans. It is also not intended that the present invention be limited to only humans. For example, animals such as horses are known to suffer from post-operative ileus. Indeed, it is a common and serious complication of colic surgery in the horse. See J. N. King and E. L. Gerring, "The Action of Low Dose Endotoxin on Equine Bowel Motility," Equine Vet. J. 23:11 (1991).

The phrase "effective amount" or "amount sufficient" is intended to mean that amount of active ingredient(s), e.g., VIP and/or PACAP receptor antagonist, which provides a therapeutic benefit in treating or preventing ileus in a patient. An example of such a therapeutic benefit is the activation or augmentation of intestinal transit in the patient being treated.

The compositions generally include a pituitary adenylate cyclase activating peptide (PACAP) receptor antagonist or a vasoactive intestinal peptide (VIP) receptor antagonist, e.g., VIP(10–28) (SEQ ID NO:2, residues 10–28). In a preferred embodiment the composition comprises both a PACAP and VIP receptor antagonist. Preferable the composition is effective at inhibiting the native peptide from binding to the following receptors: vasoactive pituitary cyclase 1 (VAPC$_1$) receptor, VPAC$_2$ receptor and pituitary adenylate cyclase 1 (PAC$_1$) receptor.

In a preferred in embodiment the VIP antagonists is a nonspecific VPAC$_1$/VAPC$_2$ receptor antagonists and the PACAP antagonist is a nonspecific PAC$_1$/VPAC$_2$ receptor. Preferably, the VIP and PACAP antagonist in the composition jointly block a VPAC$_1$, VAPC$_2$, and PAC$_1$ receptor.

The term "PACAP receptor antagonist" means a receptor antagonist with a binding coefficient for PAC$_1$/VPAC$_2$ receptors, preferably the binding coefficient is equal to or greater than the native PACAP peptide.

The native peptide sequence of PACAP is His-Ser-Asp-Gly-Ile-Phe-Thr-Asp-Ser-Tyr-Ser-Arg-Tyr-Arg-Lys-Gln-Met-Ala-Val-Lys-Lys-Tyr-Leu-Ala-Ala-Val-Leu-Gly-Lys-Arg-Tyr-Lys-Gln-Arg-Val-Lys-Asn-Lys-NH2 (SEQ ID NO:1).

Active variations of the natural PACAP peptide are well known in the art, for example, as discussed in the article by Robberecht et al in Eur. J. Biochem. 1992 Jul. 1;207(1):239–46.

Non-limiting examples of preferred PACAP receptor antagonists include PACAP(6–38) (SEQ ID NO:1, residues 6–38); PACAP(6–27) (SEQ ID NO:1, residues 6–27); analogues of PACAP receptor antagonists (SEQ ID NO:10) and combinations thereof. In one embodiment the preferred PACAP receptor antagonist comprises amino acid residues 1–3 of SEQ ID NO:1, namely His-Ser-Asp. In this embodiment, it is preferably that residues 3, 6, 7, and 23 of PACAP (SEQ ID NO:1) are conserved.

Preferably the PACAP receptor antagonist comprises the following structural description: amino acid number 1 ("AA1") is absent, His or Tyr; amino acid number 2 ("AA2") is absent, Ser, Ala or D-Arg; amino acid number 3 ("AA3") is absent, or Asp; amino acid number 4 ("AA4") is absent, Gly, Ala, or Cys; amino acid number 5 ("AA5") is absent, Ile, Val, or Thr; amino acid number 6 ("AA6") is Phe; amino acid number 7 ("AA7") is Thr; amino acid number 8 ("AA8") is Asp, Ser, Glu, or Asn; amino acid number 9 ("AA9") is Ser, Asn, Glu, or Asp; amino acid number 10 ("AA10") is Tyr, or Leu; amino acid number 11 ("AA11") is Ser, Thr, or Arg; amino acid number 12 ("AA12") is Arg or Lys; amino acid number 13 ("AA13") is Tyr, Leu, or Val; amino acid number 14 ("AA14") is Arg, Leu, or Gln; amino acid number 15 ("AA15") is Lys, Gly, Cys, Ala, or Glu; amino acid number 16 ("AA16") is Gln, Ala, Lys, or Gly; amino acid number 17 ("AA17") is Met, Leu, Ile, or Ala; amino acid number 18 ("AA18") is Ala, Ser, or Arg; amino acid number 19 ("AA19") is Val, Ala, Gln, or Leu; amino acid number 20 ("AA20") is Lys, Gln, or Arg; amino acid number 21 ("AA21") is Lys or Arg; amino acid number 22 ("AA22") is Tyr or Leu; amino acid number 23 ("AA23") is Leu; amino acid number 24 ("AA24") is Ala, Asn, Glu, or Gln; amino acid number 25 ("AA25") is Ala, Ser, Gly, or Asp; amino acid number 26 ("AA26") is Val, Ile, Leu; amino acid number 27 ("AA27") is Leu, Ile, Val, or Met; amino acid number 28 ("AA28") is Gly, absent, Asn, or Ser; amino acid number 29 ("AA29") is Lys, absent, Ser, or Arg; and amino acid number 30 ("AA30") is Arg, absent or Gln (SEQ ID NO:10).

The term "VIP receptor antagonist" means a receptor antagonist with a binding coefficient for VPAC1/VPAC2 receptors, preferably the binding coefficient is equal to or greater than the native VIP peptide.

The peptide sequence of VIP is His-Ser-Asp-Ala-Val-Phe-Thr-Asp-Asn-Tyr-Thr-Arg-Leu-Arg-Lys-Gln-Met-Ala-Val-Lys-Lys-Tyr-Leu-Asn-Ser-Ile-Leu-Asn-NH2 (SEQ ID NO:2).

Non-limiting examples of preferred VIP receptor antagonists include:
 (i) VIP(6–28) (SEQ ID NO:2, residues 6–28);
 (ii) [D-p-Cl-Phe$^6$, Leu$^{17}$]VIP (SEQ ID NO:4);
 (iii) [Tyr$^9$, Dip$^{18}$]VIP(6–23) (SEQ ID NO:5);
 (iv) [Tyr$^9$, Dip$^{18}$]VIP(6–28) (SEQ ID NO:6);
 (v) GH-releasing factor-(8–27)NH$_2$—structure description: Asn-Ser-Tyr-Arg-Lys-Val-Leu-Gly-Gln-Leu-Ser-Ala-Arg-Lys-Leu-Leu-Gln-Asp-Ile-Met-NH2 (SEQ ID NO:7);
 (vi) GHRH—structure description: Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-Gln-Gln-Gly-Glu-Ser-Asn-Gln-Glu-Arg-Gly-Ala-Arg-Ala-Arg-Leu (SEQ ID NO:11) and analogues;
 (vii) Analogues of GHRH (SEQ ID NO:12) with VIP receptor binding properties;
 (viii) [Ac-His$^1$, D-Phe$^2$, Lys$^{15}$, Arg$^{16}$, Leu$^{25}$] VIP(3–7)/GRF(8–27)—structure description: [Ac-His$^1$, D-Phe$^2$, Lys$^{15}$, Arg$^{16}$, Leu$^{25}$]-Asp-Ala-Val-Phe-Thr-Asn-Ser-Tyr-Arg-Lys-Val-Leu-Gly-Gln-Leu-Ser-Ala-Arg-Lys-Leu-Leu-Gln-Asp-Ile-Met-NH2 (SEQ ID NO:8);
 (ix) [N-Ac-Tyr$^1$, D-Phe$^2$]-GRF(1–29)NH$_2$—structure description: [N-Ac-Tyr$^1$, D-Phe$^2$]-Tyr-Ala-Asp-Ala-Ile-Phe-Thr-Asn-Ser-Tyr-Arg-Lys-Val-Leu-Gly-Gln-Leu-Ser-Ala-Arg-Lys-Leu-Leu-Gln-Asp-Ile-Met-Ser-Arg-(SEQ ID NO:9);
 (x) VIP(10–28) (SEQ ID NO:2, residues 10–28);
 (xi) VIP(11–28) (SEQ ID NO:2, residues 11–28); and
 (xii) VIP-hyb (SEQ ID NO:3)—a hybrid peptide of neurotensin and VIP consisting of an N-terminal Lys-Pro-Arg-Arg-Pro-Tyr (designed to increase membrane permeability) followed by the C-terminal 22 amino acids of VIP (SEQ ID NO:2).

Analogues of GHRH have VIP receptor binding properties and amino acid residues 3, 11, 14, 16, 17, 19, 32 are preferably conserved and more preferably residues 2, 6, 10, 15, 20, 23, 27, 33, and 37 are also conserved. In a preferred embodiment the analogue comprises the following structural description: AA1 is Tyr or His; AA2 is Ala, Val, or Ser; AA3 is Asp; AA4 is Ala, Gly, or Asp; AA5 is Ile, Leu, or Met; AA6 is Phe or Leu; AA7 is Thr, Ser, Asn, or Asp; AA8 is Asn, Ser, Thr, Lys, or Arg; AA9 is Ser, Asn, Ala, or Asp; AA10 is Tyr or Leu; AA11 is Arg; AA12 is Lys, Arg, Asp, or Asn; AA13 is Val, Ile, Leu, Ala or Tyr; AA14 is Leu; AA15 is Gly, Ser, or Val; AA16 is Gln; AA17 is Leu; AA18 is Ser, Tyr, or Arg; AA19 is Ala; AA20 is Arg or Gln; AA21 is Lys, Asn, or Arg; AA22 is Leu, Val, Tyr, or Phe; AA23 is Leu or Ile; AA24 is Gln or His; AA25 is Asp, Glu, Ser, Thr, or Trp; AA26 is Ile or Leu; AA27 is Met or Thr; AA28 is Ser, Asn, or Ala; AA29 is Arg, Lys, or Val; AA30 is Gln, Arg, or His; AA31 is Gln, Val, or Leu; AA32 is Gly; AA33 is Glu, Gly, or Ala; AA34 is Ser, Arg, Ala, Val, Gly, or Glu; AA35 is Asn, Ile, Ser, or Glu; AA36 is Gln, Ser, Met, Thr, or Glu; AA37 is Glu, Ser, Ile, Met, or Asp; AA38 is Arg, Gln, Leu, or Glu; AA39 is Gly, Arg, Glu, or Asp; AA40 is Ala, Pro, Ser, or Asp; AA41 is Arg, Lys, Glu, Asp, Asn, Thr, or Ser; AA42 is Ala, Val, Ser, Phe, Leu or absent; AA43 is Arg, Val, Asn, Ser, or Glu; AA44 is Leu, Arg, Pro, or absent (SEQ ID NO:12).

In one preferred embodiment of the composition, the VIP receptor antagonist is VIP(10–28) (SEQ ID NO:2, residues 10–28) and the PACAP receptor antagonist is PACAP(6–38) (SEQ ID NO:1, residues 6–38).

It is not intended that the present invention be limited only the peptides specifically disclosed. The PACAP and VIP antagonist disclosed herein are simply for illustrative purposes only. A variety of peptide derivatives are contemplated, including peptides where additional amino acids are added to the carboxy terminus. Alternatively, peptides are contemplated where amino acids are added to the amino terminus. The present invention contemplates peptides having the above primary structure wherein certain amino acids are substituted or deleted. The present invention also contemplates peptide derivatives having a combination of the above-described changes, such as where amino acids are added to both the amino and carboxy termini.

In another embodiment, the present invention also contemplates peptides protected from endoprotease degradation by the substitution of L-amino acids in said peptides with their corresponding D-isomers. It is not intended that the present invention be limited to particular amino acids and particular D-isomers. This embodiment is feasible for all amino acids, except glycine; that is to say, it is feasible for all amino acids that have two stereoisomeric forms. By convention these mirror-image structures are called the D and L forms of the amino acid. These forms cannot be interconverted without breaking a chemical bond. With rare exceptions, only the L forms of amino acids are found in naturally occurring proteins.

In one embodiment, mimetics are provided. Mimetics of the present invention are peptides having sequence homology to the above-described peptides, PACAP and VIP receptor antagonists and further maintain the ability to function as antagonists.

One common methodology for evaluating mimetics for sequence homology, and more importantly statistically significant similarities, is to use a Monte Carlo analysis using an algorithm written by Lipman and Pearson to obtain a Z value. According to this analysis, a Z value greater than 6 indicates probable significance, and a Z value greater than 10 is considered to be statistically significant. W. R. Pearson and D. J. Lipman, Proc. Natl. Acad. Sci. (USA), 85:2444–2448 (1988); D. J. Lipman and W. R. Pearson, Science, 227:1435–1441 (1985). In the present invention, synthetic polypeptides useful in therapy are those peptides with statistically significant sequence homology and similarity (Z value of Lipman and Pearson algorithm in Monte Carlo analysis exceeding 6), while maintaining the antagonistic function.

The composition of the invention typically comprises VIP and PACAP receptor antagonists in an amount sufficient to treat or prevent ileus in a patient. Preferably the PACAP and VIP antagonists in combination are in an amount of equal to between 0.001 and 5000 µg per kg body weight of the patient being treated or more preferably in an amount between 50 and 500 µg per kg body weight of the patient being treated.

The composition of the invention generally comprises a ratio of 10:1 to 1:10, preferably 5:1 to 1:5 and more preferably between 4:1 to 1:4, VIP-receptor antagonists to PACAP receptor antagonists by weight. In one preferred embodiment the ratio is 1:1.

Often, the composition of the invention further includes a carrier. The carrier may be any pharmaceutically suitable carrier selected on the basis of the chosen route of administration and standard pharmaceutical practice as described, for example, in Remington's Pharmaceutical Sciences (Mack Pub. Co., Easton, Pa., 1980), the disclosures of which are hereby incorporated herein by reference, in their entirety.

In one embodiment, the carrier is sterically stabilized micelles (SSM), sterically stabilized liposomes (SSL), or mixed micelles. Methods of making and using such carriers is fully taught and described in U.S. Pat. Nos. 6,217,886, 6,348,214, 6,322,810, and 6,197,333, the disclosures of which are incorporated herein by reference.

Compositions of the present invention can be administered to a patient in a variety of forms adapted to the chosen route of administration, e.g., orally or parenterally. Parenteral administration in this respect includes administration by the following routes: intravenous, intramuscular, subcutaneous, rectal, intraocular, intrasynovial, transepithelial including transdermal, ophthalmic, sublingual and buccal; topically including ophthalmic, dermal, ocular, rectal, and nasal inhalation via insufflation aerosol. In a preferred embodiment the composition is administered intravenously or orally and the patient is a human suffering from postoperative ileus or paralytic ileus. The composition is preferably administered pre-operatively, intra-operatively, post-operatively, or a combination thereof.

The active composition may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active composition may be incorporated with excipient and used in the form of ingestible tablets, buccal tablets, troches, capsules, elixirs, suspensions, syrups, wafers, and the like. Such compositions and preparations should preferably contain at least 0.1% of active composition. The percentage of the compositions and preparations may, of course, be varied and may conveniently be, for example, from about 2 to about 6% of the weight of the unit. The amount of active composition in such therapeutically useful compositions is preferably such that a suitable dosage will be obtained. Preferred compositions or preparations according to the present invention may be prepared so that an oral dosage unit form contains from about 0.1 to about 1000 mg of active composition.

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both.

A syrup or elixir may contain the active composition, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active composition may be incorporated into sustained-release preparations and formulations.

The forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active composition in the required amount, in the appropriate solvent, with various of the other ingredients enumerated above, as required, followed by filtered sterilization. Generally, dispersions may be prepared by incorporating the sterilized active ingredient into a sterile vehicle that contains the basic dispersion medium and the required other ingredients from those enumerated above. In the case of sterile powders for the preparation of sterile injectable solutions, the preferred methods of preparation may include vacuum drying and the freeze drying technique which yield a powder of the active ingredient, plus any additional desired ingredient from the previously sterile-filtered solution thereof.

As noted above, the relative proportions of active ingredient and carrier may be determined, for example, by the solubility and chemical nature of the composition, chosen route of administration and standard pharmaceutical practice.

The dosage of the compositions of the present invention that will be most suitable for prophylaxis or treatment will vary with the form of administration, the particular composition chosen and the physiological characteristics of the particular patient under treatment. Generally, small dosages may be used initially and, if necessary, increased by small increments until the desired effect under the circumstances is reached.

The present compositions may also be prepared by any of the available methods of pharmacy. In those embodiments wherein a carrier is included, the carrier with the active ingredient are brought into association by uniformly and intimately admixing the active ingredient with liquid carriers or finely divided solid carriers or both, and then, in necessary, shaping the product into the desired presentation.

It is also envisioned that controlled release means or delivery devices can be used to administer the compositions disclosed herein. These means are well known in the art, such as described in U.S. Pat. Nos. 5,345,556, 5,427,798, 5,486,362, 5,591,767, 5,639,476, 5,674,533, and 5,733,566, for example, the disclosures of which are incorporated herein by reference. The dosage forms can be used to provide slow or controlled release VIP, PACAP, or a combination thereof.

Although preferred embodiments of the invention have been described in the foregoing description, it will be understood that the invention is not limited to the specific embodiments disclosed herein but is capable of numerous modifications by one of ordinary skill in the art.

Furthermore, the invention is also described in the following example. The example, is for illustrative purposes only, and is not to be construed as limiting the appended claims.

EXAMPLE

In Vivo Study Using Male Wistar Rats

Male Wistar rats are commonly used to study the mechanisms that regulate gastrointestinal function by several laboratories across the United States and the world. This model is well characterized experimentally and has the added advantage of providing results in a short time frame, limiting the animal's distress.

Test Article Preparation Protocol

Two hours prior to start of surgery, the required amount of peptide was measured to the nearest 1 mg and placed into 0.5 ml saline. The suspension was then vortexed for 1 minute and then incubated at room temperature for one hour after. The solution was kept refrigerated until 30 minutes before the onset of surgery. The solution was allowed to warm to room temperature for 30 minutes prior to the surgery. Following this warming period, the solution was placed into a 1 cc insulin syringe for tail vein injection 1 minute prior to surgery.

Operational Protocol

Male Wistar rats (150–250 g) were fasted for 48 hours with free access to water. This fast was necessary to empty the gastrointestinal tract so that the Evans Blue introduced after the surgery could be accurately tracked. The rats were divided into groups in a randomized way. The randomized groups were then given isoflorane anesthesia, followed by clearing of the abdominal area with 10% antibacterial iodine solution and alcohol and shaving prior to surgery. Isoflorane was administered continuously (3–5%) using a vaporizer. Importantly, like ether, isoflorane has previously been shown to induce ileus (Isoflorane MSDS, Halocarbon Corp., River Edge, N.J. 07661). Diethyl ether can also be used for anesthesia.

Thereafter, the rats received an i.v. injection (VIP receptor antagonists, PACAP receptor antagonists, or combination thereof were delivered in saline) in the tail vein of the appropriate drug or control for its group one minute before the operation. The peptides included VIP (10–28) and PACAP (6–38). The dosage amount of each peptide administered was approximately 150 µg per kg body weight. For the combination treatment a ratio of 1:1 of a PACAP receptor antagonist to VIP receptor antagonists was used, the total peptide amount being approximately 300 µg per kg body weight. The peptide dosages were consistent animal to animal throughout the study and were administered by bolus injections.

All groups underwent a laparotomy consisting of the incision of the abdominal skin, abdominal muscle layers and peritoneum. The laparotomy was followed by evisceration and manipulation of the small intestine and the caecum. In these experiments, the caecum and small intestine were gently pulled out of the abdominal cavity, unfurled like a fan and exposed on two sterile gauzes covering the abdomen of the rat. Following this, the caecum and the small intestine were gently touched by the fingers starting from the caecum up to the duodenal end of the small intestine. This procedure was repeated three times during a five-minute period.

This manipulation of the intestines and the use of anesthetic were used to induce POI. The caecum and small intestine were replaced in the abdominal cavity and the suture closed. Several drops of bupivicaine was placed at the suture site to provide local anesthetic following the surgery. [Method taken from Benedicte et al., Brit J Pharm; 1998]

Following the operation, the rats were allowed to recover for one hour, followed by an oral administration of 0.1 ml Evans blue (50 mg in 1 ml 0.9% sodium chloride) via an orogastric cannula introduced through the mouth into the stomach. [Method taken from Benedicte et al., Brit J Pharm; 1998]

Twenty minutes later, the rats were euthanized by an overdose pentobarbital (150 mg/kg i.v. tail vein) and the intestinal transit was measured from the pylorus to the most distal point of the migration of Evans blue and expressed in cm.

Materials

Isofluorane; Evan's Blue; 5% iodine solution; vasoactive intestinal peptide; vasoactive intestinal peptide (10–28); PACAP; PACAP (6–38); saline; and alcohol wipes.

Data Analysis

Figure 1:
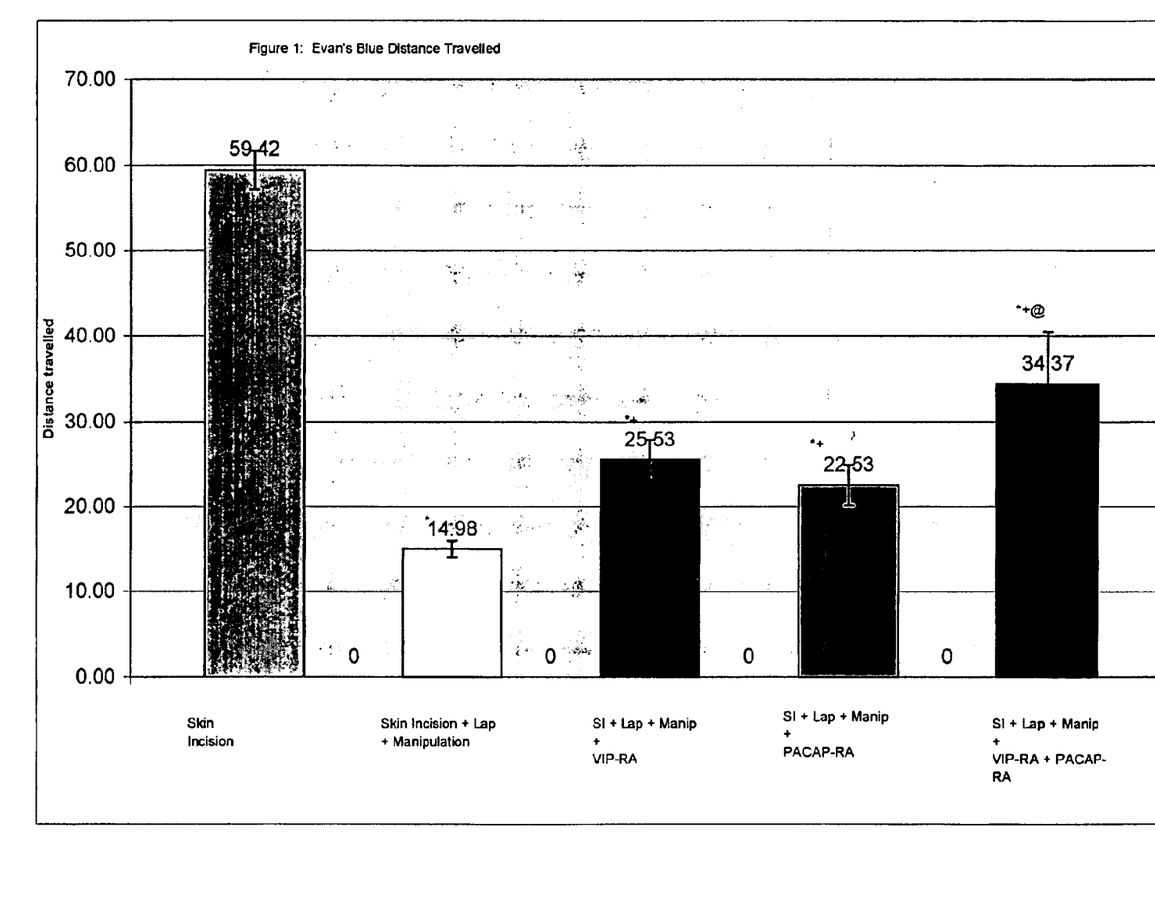
FIG. 1 shows the effect of receptor antagonists on the distance Evan's Blue traveled through Wistar rat intestines.
Figure 2:
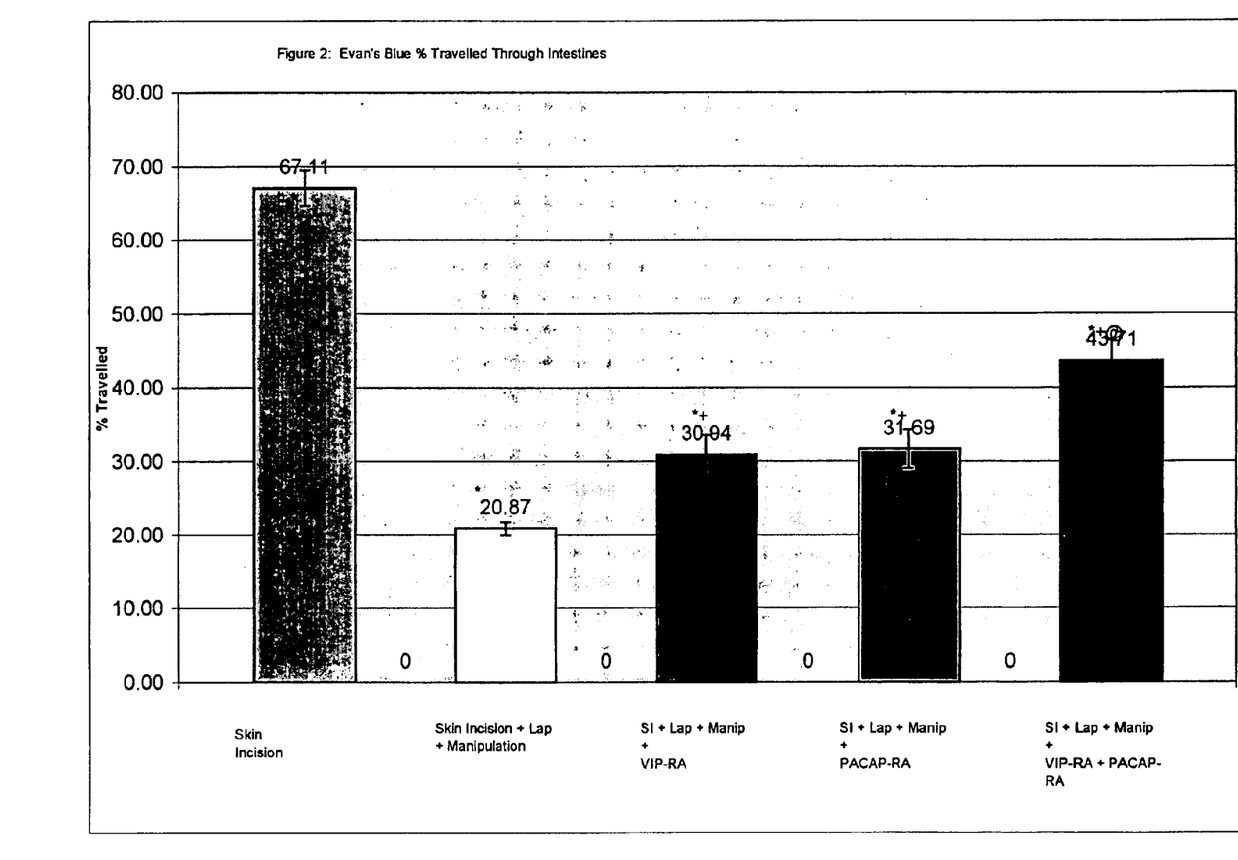

As can be seen in FIGS. 1 and 2, following anesthesia, skin incision alone had very little effect on intestinal transit. During the 20 minute transit period, Evan's Blue was moved through the intestines an average distance of 59 cm (67% of the total distance of the intestines). As previously described, the addition of a laparatomy and manipulation of the intestines to the skin incision drastically reduced the motility of the intestines. Evan's Blue only traveled a distance of 15 cm (21% of the total distance of the intestines).

The use of both VIP and PACAP receptor antagonists individually prior to the start of surgery both significantly increased intestinal motility. VIP-RA increased intestinal motility to 26 cm (31% of the intestinal length). PACAP-RA increased intestinal motility to 23 cm (32% of the intestinal length).

The use of VIP and PACAP receptor antagonists in combination, however, surprisingly resulted in significantly increased intestinal motility then the use of either antagonists used separately. Statistically, the combined receptor antagonist therapy not only significantly increased intestinal motility versus no treatment, but also significantly increased intestinal motility when compared to treatment with either receptor antagonist alone. As can be seen in FIGS. 1 and 2, intestinal motility was increased to an average distance of 34 cm (44% of the intestinal length).

Given these findings, it is clear that the combined receptor antagonist treatment is able to significantly increase intestinal motility in male Wistar rats following abdominal surgery. Surprisingly, the combination of VIP and PACAP receptor antagonists are more effective than a similar dosage of VIP receptor antagonists or PACAP receptor antagonist administered alone. This increase is most likely due to the ability of the two receptor antagonists to block the effects of VIP and PACAP, released during the surgery in the intestines, to bind with their respective PAC1, VPAC1 and VPAC2 receptors.

Although preferred embodiments of the invention have been described in the foregoing description, it will be understood that the invention is not limited to the specific embodiments disclosed herein but is capable of numerous modifications by one of ordinary skill in the art. It will be understood that the materials used and the details may be slightly different or modified from the descriptions herein without departing from the compositions and methods of treatment and prevention disclosed and taught by the present invention.

What is claimed is:

1. A pharmaceutical receptor antagonists composition for treating or reducing ileus in a patient consisting of:
a pituitary adenylate cyclase activating peptide (PACAP) receptor antagonist and a vasoactive intestinal peptide (VIP) receptor antagonist, wherein the PACAP receptor antagonist and VIP receptor antagonist are in an amount sufficient to treat or reduce ileus and at least one pharmaceutical acceptable ingredient.

2. The pharmaceutical receptor antagonists composition of claim 1, wherein the PACAP and VIP receptor antagonists inhibit a vasoactive pituitary cyclase 1 (VPAC1) receptor, a VPAC2 receptor and a pituitary adenylate cyclase 1 (PAC1) receptor.

3. The pharmaceutical receptor antagonists composition of claim 1, wherein the pharmaceutical ingredient is selected from the group consisting of: an exipient, diluent, binder, lubricant, sweetening agent, flavoring agent, coating agent, preservative dye, surfactant, absorption delaying agent; and a carrier.

4. The pharmaceutical receptor antagonists composition of claim 3, wherein the carrier is a sterically stabilized micelles (SSM), a sterically stabilized liposomes (SSL), or mixed micelles.

5. The pharmaceutical receptor antagonists composition of claim 1, wherein the PACAP receptor antagonist is selected from the group consisting of PACAP(6–38) (SEQ ID NO:1, residues 6–38), PACAP(6–27) (SEQ ID NO:1, residues 6–27), analogues of PACAP receptor antagonists (SEQ ID NO:10), and combinations thereof.

6. The pharmaceutical receptor antagonists composition of claim 1, wherein the VIP receptor antagonist is selected from a group consisting of VIP(6–28) (SEQ ID NO:2, residues 6–28), VIPhyb (SEQ ID NO:3), [D-p-Cl-Phe$^6$, Leu$^{17}$]VIP (SEQ ID NO:4), [Tyr$^9$, Dip$^{18}$]VIP(6–23) (SEQ ID NO:5), [Tyr$^9$, Dip$^{18}$]VIP(6–28) (SEQ ID NO:6), GH-releasing factor-(8–27)NH$_2$ (SEQ ID NO:7), GHRH analogues with VIP receptor binding properties (SEQ ID NO:12), [Ac-His$^1$, D-Phe$^2$, Lys$^{15}$, Arg$^{16}$, Leu$^{25}$]VIP(3–7)/GRF(8–27) (SEQ ID NO:8), [N-Ac-Tyr$^1$, D-Phe$^2$]-GRF(1–19)NH2 (SEQ ID NO:9), VIP(10–28) (SEQ ID NO:2, residues 10–28), VIP(11–28) (SEQ ID NO:2, residues 11–28), [Ac-Try$^1$, D-Phe$^2$]-GRF(1–29) amide (SEQ ID NO:9), and combinations thereof.

7. The pharmaceutical receptor antagonists composition of claim 1, wherein the VIP antagonist is VIP(10–28) (SEQ ID NO:2, residues 10–28), and the PACAP antagonist is PACAP(6–38) (SEQ ID NO:1, residues 6–38).

8. A method for treating or reducing ileus in a patient comprising:
administering to a patient in need of such treatment the pharmaceutical receptor antagonists composition of claim 1 in an amount effective to activate or augment intestinal transit in the patient.

9. The method of claim 8, wherein the patient is suffering from postoperative ileus, post-partum ileus, or paralytic ileus.

10. The method of claim 9, wherein the patient is human and the amount of PACAP and VIP antagonists in combination is between 50 and 500 μg per kg body weight of the patient being treated.

11. The method of claim 8, wherein the PACAP and VIP receptor antagonists inhibit a vasoactive pituitary cyclase 1 (VPAC1) receptor; a VPAC2 receptor and a pituitary adenylate cyclase 1 (PAC1) receptor.

12. The method of claim 8, wherein the ingredient is selected from the group consisting of: an excipient, diluent, binder, lubricant, sweetening agent, flavoring agent, coating agent, preservative, dye, surfactant, absorption delaying agent; and a carrier.

13. The method of claim 12, wherein the carrier is a sterically stabilized micelles (SSM); a sterically stabilized liposomes (SSL); or mixed micelles.

14. The method of claim 8, wherein the PACAP receptor antagonist is selected from a group consisting of PACAP (6–38) (SEQ ID NO:1, residues 6–38); PACAP(6–27) (SEQ ID NO:1, residues 6–27); analogues of PACAP receptor antagonists (SEQ ID NO:10) and combinations thereof.

15. The method of claim 8, wherein the VIP receptor antagonist is selected from a group consisting of VIP(6–28) (SEQ ID NO:2, residues 6–28); VIPhyb (SEQ ID NO:3); [D-p-Cl-Phe$^6$, Leu$^{17}$]VIP (SEQ ID NO:4); [Tyr$^9$, Dip$^{18}$]VIP (6–23) (SEQ ID NO:5); [Tyr$^9$, Dip$^{18}$]VIP(6–28) (SEQ ID NO:6); GH-releasing factor-(8–27)NH$_2$ (SEQ ID NO:7); GHRH analogues with VIP receptor binding properties (SEQ ID NO:12); [Ac-His$^1$, D-Phe$^2$, Lys$^{15}$, Arg$^{16}$, Leu$^{25}$] VIP(3–7)/GRF(8–27) (SEQ ID NO:8); [N-Ac-Tyr$^1$, D-Phe$^2$]-GRF(1–29)NH$_2$ (SEQ ID NO:9); VIP(10–28) (SEQ ID NO:2, residues 10–28); VIP(11–28) (SEQ ID NO:2, residues 11–28); [Ac-Try$^1$, D-Phe$^2$]-GRF(1–29) amide (SEQ ID NO:9); and combinations thereof.

16. The method of claim 8, wherein the VIP receptor antagonist is VIP(10–28) (SEQ ID NO:2, residues 10–28) and the PACAP receptor antagonist is PACAP(6–38) (SEQ ID NO:1, residues 6–38).

17. The method of claim 8, wherein the PACAP and VIP antagonists in combination are administered in an amount equal to between 50 μg and 500 μg per kg body weight of the patient being treated.

18. The method of claim 8, wherein the antagonist is administered intravenously, intra-arterially, intra-nasally, aerosol administration, nebulization, inhalation, insufflation, intratracheally, intraarticularly, orally, transdermally, subcutaneously, or topically onto mucous membranes.

19. The method of claim 8, wherein the patient is a human suffering from postoperative ileus, post-partum ileus, or paralytic ileus.

20. The method of claim 8, wherein the pharmaceutical receptor antagonists composition is administered pre-operatively, intra-operatively, post-operatively, or a combination thereof.

* * * * *